United States Patent
Finkenzeller et al.

[11] Patent Number: 5,954,667
[45] Date of Patent: Sep. 21, 1999

[54] DEVICE FOR DERIVING ACOUSTICALLY EVOKED BRAIN POTENTIALS

[76] Inventors: Peter Finkenzeller, Loewenichstrasse 6 B, 91054 Erlangen; Claudia Kammermeier-Blessing, Am Lindenberg 25, 89438 Holzheim-Eppisburg, both of Germany

[21] Appl. No.: 08/924,653

[22] Filed: Sep. 5, 1997

[30] Foreign Application Priority Data

Sep. 7, 1996 [DE] Germany ............... 296 15 656 U

[51] Int. Cl.[6] ........................................... A61B 5/04
[52] U.S. Cl. ............................... 600/544; 600/559
[58] Field of Search .......................... 600/544, 545, 600/559

[56] References Cited

U.S. PATENT DOCUMENTS

| | | | |
|---|---|---|---|
| 3,799,146 | 3/1974 | John et al. | 600/544 |
| 4,029,083 | 6/1977 | Baylor | 600/559 |
| 4,493,327 | 1/1985 | Bergelson et al. | 600/544 |
| 4,706,679 | 11/1987 | Schmidt et al. | 600/386 |
| 5,197,332 | 3/1993 | Shennib | 600/559 |
| 5,282,475 | 2/1994 | Urbach et al. | 600/559 |
| 5,495,853 | 3/1996 | Yasushi | 600/545 |
| 5,601,091 | 2/1997 | Dolphin | 600/544 |
| 5,678,559 | 10/1997 | Drakulic | 600/544 |
| 5,697,379 | 12/1997 | Neely et al. | 600/544 |
| 5,755,230 | 5/1998 | Schmidt et al. | 600/544 |

*Primary Examiner*—Cary O'Connor
*Assistant Examiner*—Charles Marmor, II
*Attorney, Agent, or Firm*—Oliff & Berridge, PLC

[57] ABSTRACT

Device for derivation of acoustically evoked brain potentials, with an electrode unit (2) on which electrodes (21, 22) are arranged relatively rigidly in the correct positions with respect to one another, and with an electroacoustic stimulator with an EEG amplifier (40) preferably also being mounted on the electrode unit, that can be simply held as a unit on the head of a subject.

20 Claims, 3 Drawing Sheets

DEVICE FOR DERIVING ACOUSTICALLY EVOKED BRAIN POTENTIALS

BACKGROUND OF THE INVENTION

The derivation of acoustically evoked electrical brain potentials is a known audiometric diagnostic method for testing hearing and for evaluating various causes of hearing damage without the active participation of the subject.

This method is referred to in the field as ERA (electric response audiometry) or BERA (brainstem electric response audiometry) or brainstem audiometry. Areas of application for this method include for example the performance of the first hearing tests in newborns, testing the hearing of infants or of unconscious persons such as accident victims for example, and the diagnosis of neurologic diseases, for example neurinomas of the acoustic nerve. Intraoperative hearing tests are also possible with this method.

Electrical brain potentials are triggered by acoustic stimulation of the ear with conduction through air or bone. Headphones are usually used for the purpose. The electrical signals that are thus generated by the brainstem are picked up by electrodes applied to the head. Usually three electrodes are used, namely one electrode to determine the reference potential and two active electrodes to derive the acoustically-evoked electrical signals at two different locations on the head.

Acoustic stimulation of the ear takes the form of click stimuli or, for direct determination of the hearing threshold, of a rapid sequence of clicks with increasing volume. The brainstem generates potential waves at each click which are averaged after being picked up and conducted away by the electrodes.

Previously, the electrodes were usually glued or attached mechanically in some other fashion individually to the head. Firstly, this is time-consuming and secondly, it imposes a stress on the patient. The cable connection also poses a risk of improper connection. In addition, the system is subjected to electrical stray fields; this is critical because of the extremely low signal potentials that must be detected. In addition, gluing the electrodes to the sensitive skin of newborns or infants and their subsequent removal is also a problem.

The combination of several electrodes into a single relatively rigid arrangement that can be mounted as a whole on the head of a person is known from U.S. Pat. No. 4,706,679 for the purpose of electroencephalography. In that patent, a frame is provided with a plurality of spring-loaded legs that have electrodes at their ends, and serves to pick up electrical brain potentials. In the known system, the frame is designed especially for mounting on the back of a patient chair in which the patient lies for the electroencephalogram. However, this prior art provides no suggestion for performing brainstem audiometry using electrodes combined in such fashion with an acoustic stimulator and a signal generator that produces the stimulating signal, or for deriving and evaluating the evoked brainstem signals.

It is therefore an object of the invention to provide a device to permit simpler and faster detection of brain potentials while performing brainstem audiometry, especially in small children.

This object is achieved according to the invention by the device described in the claims.

SUMMARY OF THE INVENTION

In the device according to the invention, the electrodes are combined into a relatively rigid arrangement that is attached by the operator manually to the head of the subject or otherwise attached as a whole to the head, and an acoustic converter in the form of a loudspeaker, an "ear bud," a bone-conduction earpiece, or an OAE probe (probe for otoacoustic emissions) is connected with the device and serves as the source of the stimuli. The device feeds the stimulator with appropriate signals to generate the series of clicks that serves for acoustic stimulation and, by using the electrode arrangement, the electrical brain potentials evoked as a result are picked up and evaluated in the device. The device according to the invention is especially advantageous in infants, for whom the examination usually takes place when they are asleep, since the application and removal of the electrodes in particular require no special manipulation and so measurement on the subject, an infant for example, is completed within a much shorter time than was previously possible.

Preferably the electrode unit also contains as integrated components the acoustic converter that serves as the stimulator in the form of a loudspeaker or a bone-conduction sound source.

In the device according to the invention, the electrode unit can also include an electroencephalograph ("EEG") amplifier as a component, so that a minimum conduction path is provided between the pickup electrodes and the EEG amplifier, and thus the possibility of stray potentials being picked up is minimized.

DETAILED DESCRIPTION OF THE INVENTION

The device according to the invention will now be described briefly in terms of its important details, with reference to the embodiments shown in the enclosed drawings.

Figure 1:
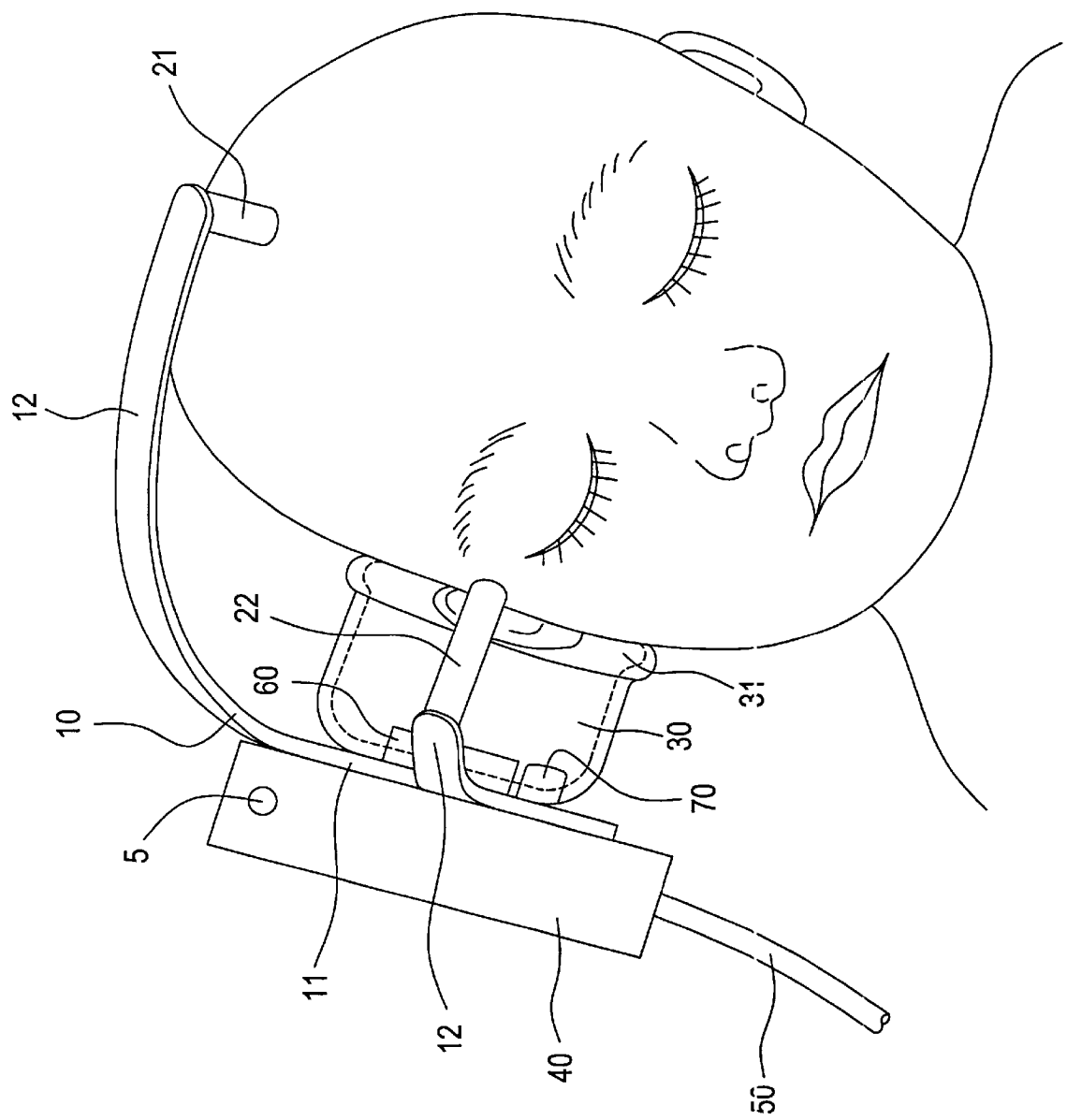
FIG. 1 shows one embodiment of the device with a loudspeaker capsule integrated into, and mounted on, the electrode unit.

The device according to FIG. 1 consists of a frame 10 with a central piece 11 and a plurality of arms 12 that have electrodes 21, 22 at their ends, a earphone 30 fastened to the central piece 11 of the frame, and an EEG amplifier 40 likewise mounted on central piece 11 of the frame on the side of said frame that faces away from the earphone.

A cable 50 connects the device with the rest of the audiometer used for brainstem audiometry, said audiometer generating the clicks for acoustic stimulation of the ear and processing and evaluating the derived brainstem potentials. In the embodiment, a single cable 50 is shown that can contain both a line to supply electrical click signals and also a line to conduct the preamplified brainstem potentials from EEG amplifier 40. Of course, separate cables or wireless transmission pathways can also be used for the purpose.

Earphone 30 preferably consists of transparent plastic and advantageously has a soft edge bead 31 for fitting tightly against the area of the head surrounding the ear. In earphone 30, an electroacoustic sound converter 60, in other words a loudspeaker, is incorporated. Instead of earphone 30 with loudspeaker 60, or in addition thereto, the device can be equipped with a bone conduction earpiece so that acoustic stimulation of the ear can take place either by conduction through air or conduction through bone.

The electrical potentials generated in the brainstem by acoustic stimulation of the ear are picked up by the electrodes on arms 12 of frame 10. Usually three electrodes are used, namely a reference electrode for detecting a reference potential and two pickup electrodes. The reference electrode is brought into contact with the head in front of the ear, and one of the two deriving electrodes is placed behind the ear and the other in the area of the crown of the head.

In the embodiment according to FIG. 1, electrode 21 is the pickup electrode that detects brainstem potentials in the vicinity of the crown of the head and electrode 22 is the reference electrode. The second pickup electrode that is applied to the head behind the ear is covered by earphone 30 in the drawing and is not visible.

In the embodiment shown, all of the electrodes are located outside earphone 30. However, it is also possible to locate the reference electrode and the pickup electrode normally located behind the ear, inside earphone 30 which is then made correspondingly larger.

Earphone 30, as already stated, preferably consists of transparent material so that both the covered ear as well as loudspeaker 60 incorporated into the earphone are visible externally, and thus the operator can check that earphone 30 is correctly positioned, namely in such fashion that the sound emitted by loudspeaker 60 is actually entering the auditory canal of the covered ear.

Earphone 30 with an ear cushion has the advantage that stimulation of the ear by means of loudspeaker 60 takes place with exclusion of ambient noise. Using earphone 30 also makes it possible to mount a microphone 70 inside earphone 30 as well, said microphone measuring the sound pressure in the earphone. As a result, during evaluation, the acoustic signal presented to the ear as an actual value signal can be checked and related directly to the time and quantity of the brainstem potentials picked up as a reaction. At the same time, the influence of any ambient noises penetrating earphone 30 can be measured.

Earphone 30 is of course adapted in terms of its shape and orientation to the elongated shape of the ear and its spatial orientation relative to the measuring points for the brainstem potentials. In order to make it possible to use the device for both the left and right ears, earphone 30 is preferably mounted rotatably on frame 10 so that its orientation relative to the frame can be adjusted as required for the right or left ear.

Figure 2:
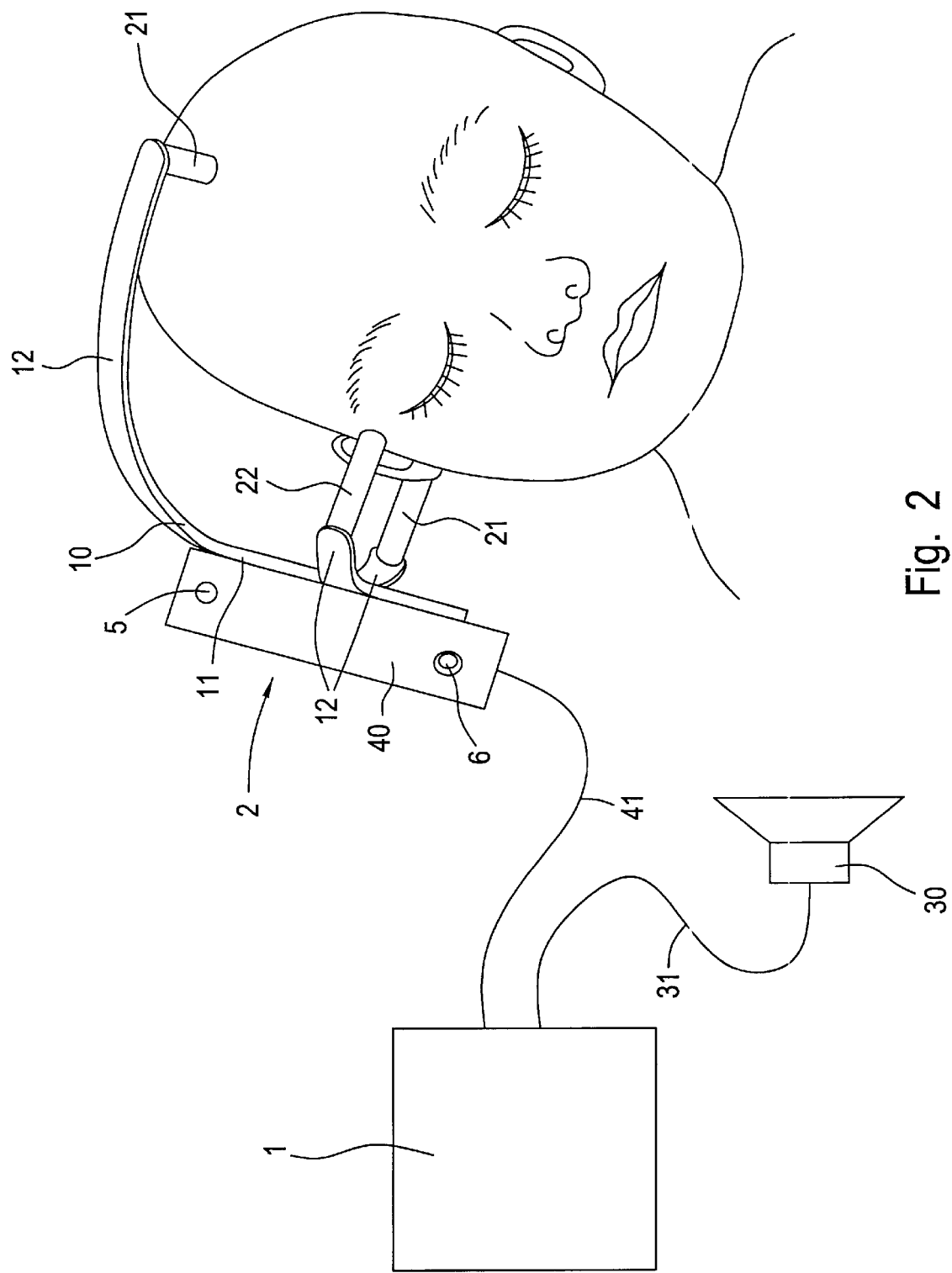
FIG. 2 shows one embodiment of the device with a free-field loudspeaker.
Figure 3:
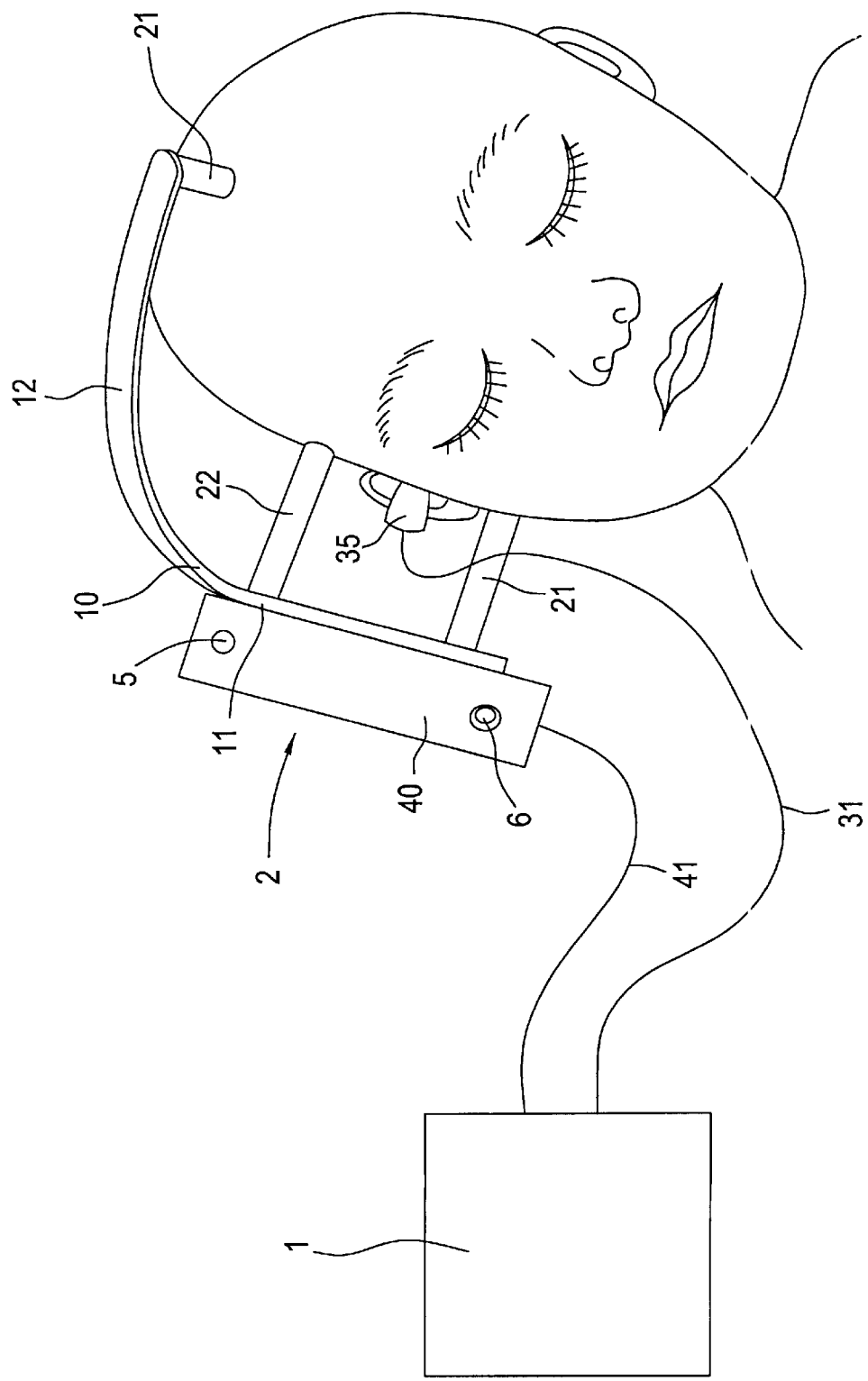
FIG. 3 shows an embodiment of the device with an "ear bud" or OAE probe.

The device according to FIGS. 2 and 3 consists of a signal generator/signal evaluation unit 1, an electrode unit 2, and a stimulator 30 or 35.

Electrode unit 2 consists of a frame 10 with a central piece 11 and arms 12 that bear electrodes 21 and 22, as well as an EEG amplifier 40 likewise mounted on central piece 11 of the frame on its side facing away from the electrodes.

A cable 41 connects the EEG amplifier and thus electrode unit 2 with a signal generator/evaluation unit 1 that is also connected by a cable 31 with stimulator 30 or 35.

Signal generator/evaluation unit 1 generates and transmits electrical stimulation signals to stimulator 30 or 35, which the latter converts into a series of acoustic clicks and then transmits them. Electrode unit 2 mounted on the head of the subject picks up the potentials evoked by the brainstem, which are then amplified by EEG amplifier 40 and fed to signal generator/evaluation unit 1 where they are evaluated.

Electrode unit 2 also has three electrodes. One of them serves as reference electrode 22.

In the embodiment according to FIG. 2, electrode unit 2 on frame 10 has several arms 12 and the electrodes are each located at the ends of these arms 12. Electrode 22 is positioned so that when the electrode unit is fitted, it comes into contact with the head in front of the ear. The other two electrodes that serve as pickup electrodes are arranged so that when the electrode unit is applied, they are brought into contact with the head in the area of the crown of the head or behind the ear.

The stimulator in the embodiment according to FIG. 2 is in the form of a free-field loudspeaker 30 that radiates the converted series of clicks into space.

The embodiment according to FIG. 3 initially shows one possible version of electrode unit 2. Here, in contrast to the embodiment shown in FIGS. 1 and 2, all the electrodes of the electrode unit are arranged approximately in a line, so that central piece 11 of frame 10 requires no arms 12 extending out to the sides. Reference electrode 22 is located between the two pickup electrodes 21. The electrodes can be spring-mounted.

In addition, FIG. 3 shows possible alternative embodiments regarding the stimulator shown in FIG. 2. Element 35 labeled as the stimulator in FIG. 3 can be an "ear bud" that produces the series of clicks directly in the ear. An "ear bud" is a plug-shaped headphone that fits into an ear canal.

Another alternative embodiment consists in the fact that the stimulator, designed as an "ear bud" serves at the same time as an auditory canal electrode and therefore also serves to pick up signals, replacing one of electrodes 21 or acting in addition thereto.

As another alternative embodiment, the stimulator simply shown schematically as element 35 in FIG. 3 can be an OAE probe, in other words a probe for otoacoustic emissions. A probe of this kind contains a loudspeaker as well as a microphone. It generates acoustic signals directly in the ear and measures the acoustic echoes, likewise in the ear, that the external hair cells in the cochlea produce. The use of an OAE probe as a stimulator thus permits a series of different measurements during one session.

Another embodiment of the stimulator that is not shown separately consists in using a bone conduction earphone, as is known of itself.

The housing of EEG amplifier 40 in all the embodiments also permits the operator to grip and hold electrode unit 2 during use. Frame 10 forms a relatively rigid system with a defined mutual position of the electrodes for potential pickup, simultaneously ensuring a certain degree of flexibility. It goes without saying that the contact surfaces of the electrodes can be provided if necessary with a suitable medium to reduce the resistance between the skin and the electrode.

A display is also advantageously provided on the housing of EEG amplifier 40 or on frame 10 of the electrode unit, for example a luminous display 5 that indicates the operational readiness and/or the functioning of the device, as well as a finger-operable switch 6 for triggering the generation of the sequence of clicks and the measuring process of the device when the operator holds the electrode unit on the subject's head.

In practice, the electrode unit can be made in various standard sizes for use with infants, children, or adult subjects.

Instead of only EEG amplifier 40, the complete device for measuring the derived brain potentials can be mounted on the frame of electrode unit 2. Signal transmission between electrode unit 2 and signal generator/evaluation unit 1 can also be performed without wires instead of using the cable connection shown in the embodiment. In addition, the series of stimulating clicks and the acquisition of measured values can be triggered in a wireless fashion by operating a switch on the electrode unit.

What is claimed is:

1. A device for deriving acoustically evoked brain potentials in brainstem audiometry from electrodes applied to a head of a subject, the device comprising:
   a plurality of electrodes comprising at least one pickup electrode and a reference electrode, to be applied to different points on the head;
   a frame that holds all of the plurality of electrodes relative to one another in a substantially fixed spatial orientation;
   the frame permitting manual or mechanical holding of the device on the head of the subject while simultaneously applying all of the plurality of electrodes to corresponding pickup points on the head;
   at least one electroacoustic converter, the frame also holding the at least one electroacoustic converter, which serves as a stimulator for acoustic stimulation of an ear.

2. The device according to claim 1, wherein the at least one electroacoustic converter comprises a loudspeaker and an earphone, the loudspeaker is mounted in the earphone, and the earphone is insulated against ambient noise.

3. The device according to claim 2, wherein the earphone comprises a microphone, and the microphone measures sound pressure in the earphone.

4. The device according to claim 2, wherein the earphone is a single earphone that is mounted rotatably on the frame, so that the relative orientation of the earphone and the plurality of electrodes can be adjusted to permit use of the device on a left ear or a right ear of the head of the subject.

5. The device according to claim 2, wherein the earphone comprises transparent material.

6. The device according to claim 2, wherein the plurality of electrodes comprises:
   a first electrode that is provided for potential derivation, and which is mounted on the frame so as to be applied to the head in a vicinity of a crown of the head;
   a second electrode that is provided for potential pickup, and which is mounted on the frame so as to be applied to the head in a head area behind the ear; and
   a third electrode that is provided as a reference electrode, and which is mounted on the frame so as to be applied to the head in a head area in front of the ear.

7. The device according to claim 6, wherein the second electrode and the third electrode are located within the earphone.

8. The device according to claim 1, wherein the at least one electroacoustic converter comprises a bone conduction earphone.

9. The device according to claim 1, for use on both ears of the head of the subject, wherein the at least one electroacoustic converter consists of two electroacoustic converters, at least one of the two electroacoustic converters comprises an earphone, and a different subset of the plurality of electrodes is associated with each of the two electroacoustic converters.

10. The device according to claim 1, wherein an EEG amplifier is mounted on the frame.

11. The device according to claim 10, wherein the entire device is mounted on the frame.

12. The device according to claim 11, further comprising a device for wireless transmission of detected signals or measured values.

13. The device according to claim 1, wherein the plurality of electrodes are mounted on the frame in an approximately linear arrangement.

14. A device for deriving acoustically evoked brain potentials in brainstem audiometry from electrodes applied to a head of a subject, the device comprising:
   an electrode unit comprising a plurality of electrodes;
   a frame that holds all of the plurality of electrodes relative to one another in a substantially fixed spatial orientation;
   the frame permitting retention, manually or mechanically, of the electrode unit on the head of the subject while simultaneously applying all of the plurality of electrodes to corresponding derivation points on the head of the subject; and
   the plurality of electrodes comprising at least one pickup electrode and a reference electrode, to be applied to different points on the head;
   an electrode converter, which acts as a stimulator for acoustic stimulation of an ear, comprising a free-field loudspeaker, an "ear bud," a probe for otoacoustic emissions that contains a loudspeaker, or a bone conduction earphone; and
   a signal generator/evaluation unit that connects the electrode unit and the electroacoustic converter, supplies the electroacoustic converter with electrical stimulation signals, and evaluates the potentials picked up by the electrodes.

15. The device according to claim 14, wherein the "ear bud" is an auditory canal electrode, which serves, in addition to the plurality of electrodes on the electrode unit, as a second pickup electrode or a second reference electrode.

16. The device according to claim 14, wherein the plurality of electrodes consists of a first electrode, a second electrode, and a third electrode, and
   the first electrode is provided for potential pickup and is mounted on the frame so as to be applied to the head in a vicinity of a crown of the head;
   the second electrode is provided for potential derivation and is mounted on the frame so as to be applied to the head in a head area behind the ear; and
   the third electrode is provided as a reference electrode and is mounted on the frame so as to be applied to the head in a head area in front of the ear.

17. The device according to claim 14, wherein an EEG amplifier is mounted on the frame of the electrode unit.

18. The device according to claim 17, wherein the entire device is mounted on the frame of the electrode unit.

19. The device according to claim 18, wherein the electrode unit further comprises a device for wireless transmission of picked-up signals or measured values to the signal generator/evaluation unit.

20. The device according to claim 14, wherein the plurality of electrodes are arranged on the frame in an approximately linear arrangement.

* * * * *